United States Patent
Rowe et al.

(10) Patent No.: US 10,352,845 B2
(45) Date of Patent: Jul. 16, 2019

(54) METHODS AND SYSTEMS FOR MAINTAINING OPTICAL TRANSPARENCY DURING PARTICLE IMAGE ACQUISITION

(71) Applicant: Halliburton Energy Services, Inc., Houston, TX (US)

(72) Inventors: Mathew Dennis Rowe, Lafayette, LA (US); Jon Troy Gosney, Bellville, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/826,502

(22) Filed: Nov. 29, 2017

(65) Prior Publication Data

US 2018/0080864 A1    Mar. 22, 2018

Related U.S. Application Data (63) Continuation of application No. 14/904,215, filed as application No. PCT/US2015/020348 on Mar. 13, 2015, now Pat. No. 9,857,289.

(51) Int. Cl.
*H04N 7/18* (2006.01)
*G01N 21/15* (2006.01)
(Continued)

(52) U.S. Cl.
CPC .......... *G01N 21/15* (2013.01); *E21B 47/0002* (2013.01); *G01N 15/0227* (2013.01);
(Continued)

(58) Field of Classification Search
CPC .................................................. G01N 27/83
(Continued)

(56) References Cited

U.S. PATENT DOCUMENTS 3,562,535 A    2/1971    Leger, Jr. et al.
6,354,734 B1    3/2002    Curran et al.
(Continued)

FOREIGN PATENT DOCUMENTS

DE    20221683 U1    12/2006
EP    0413761 A1    2/1991
EP    1867833 A1    12/2007

OTHER PUBLICATIONS

Saasen et al., "Automatic Measurement of Drilling Fluid and Drill-Cuttings Properties," SPE Drilling and Completion, Dec. 2009.
(Continued)

*Primary Examiner* — Anand S Rao
(74) *Attorney, Agent, or Firm* — Gilliam IP PLLC (57) ABSTRACT

Fouling of or damage to an electromagnetic radiation-transparent window can preclude one from obtaining satisfactory images with an image acquisition unit, such as a camera. Certain types of environments may be particularly prone toward promoting fouling or damage, and manual cleaning or repair of an electromagnetic radiation-transparent window may be difficult in some circumstances. These issues may be particularly prevalent when imaging drill cuttings and other solids obtained from a wellbore due to the complex sampling environment in which these solids are often disposed. Wellhead imaging systems can comprise: a flow pathway extending from a wellbore; an electromagnetic radiation-transparent window external to the wellbore establishing optical communication with the flow pathway; an image acquisition unit in optical communication with the flow pathway via the electromagnetic radiation-transparent window; and a movable barrier that is also electromagnetic radiation-transparent and is disposed between the electro-
(Continued)

magnetic radiation-transparent window and the flow pathway.

20 Claims, 3 Drawing Sheets (51) Int. Cl.
G01N 15/02 (2006.01)
G02B 27/00 (2006.01)
E21B 47/00 (2012.01)
G01N 15/14 (2006.01)
G01V 8/02 (2006.01)
H04N 5/33 (2006.01)
G01N 15/00 (2006.01)

(52) U.S. Cl.
CPC ........... *G01N 15/1459* (2013.01); *G01V 8/02* (2013.01); *G02B 27/0006* (2013.01); *H04N 5/332* (2013.01); *G01N 2015/0053* (2013.01); *G01N 2021/152* (2013.01); *G01N 2021/157* (2013.01)

(58) Field of Classification Search
USPC ...................................... 348/85–86, 164–167
See application file for complete search history.

(56) References Cited

U.S. PATENT DOCUMENTS

| | | |
|---|---|---|
| 6,630,947 B1 | 10/2003 | Lieberman et al. |
| 2006/0102346 A1 | 5/2006 | Casey |
| 2007/0035736 A1 | 2/2007 | Vannuffelen et al. |
| 2007/0194947 A1 | 8/2007 | Huang et al. |
| 2009/0288820 A1 | 11/2009 | Barron et al. |
| 2010/0097450 A1 | 4/2010 | Pugh et al. |
| 2010/0101437 A1 | 4/2010 | Bauernfeind |
| 2010/0258304 A1 | 10/2010 | Hegeman |
| 2012/0093300 A1 | 4/2012 | Mann et al. |
| 2013/0258472 A1 | 10/2013 | Ritzl |
| 2014/0333754 A1 | 11/2014 | Graves et al. |
| 2015/0138557 A1 | 5/2015 | Tjhang et al. |
| 2016/0252481 A1* | 9/2016 | Zheng et al. .......... G01N 27/83 348/85 |
| 2017/0108428 A1 | 4/2017 | Rowe et al. |

OTHER PUBLICATIONS

International Search Report and Written Opinion from PCT/US2015/020348, dated Nov. 30, 2015.

Search Report from Belgium Application No. 2016/5037, dated Aug. 26, 2016.

* cited by examiner

METHODS AND SYSTEMS FOR MAINTAINING OPTICAL TRANSPARENCY DURING PARTICLE IMAGE ACQUISITION

CROSS-REFERENCE TO RELATED APPLICATIONS

The present application claims the benefit of priority under 35 U.S.C. § 120 as a continuation from U.S. patent application Ser. No. 14/904,215, entitled "METHODS AND SYSTEMS FOR MAINTAINING OPTICAL TRANSPARENCY DURING PARTICLE IMAGE ACQUISITION," filed Jan. 11, 2016, which is a National Stage entry of and claims priority to PCT Application No. PCT/US2015/020348, entitled "METHODS AND SYSTEMS FOR MAINTAINING OPTICAL TRANSPARENCY DURING PARTICLE IMAGE ACQUISITION," filed on Mar. 13, 2015, the disclosures of which are hereby incorporated by reference in their entirety for all purposes.

BACKGROUND

The present disclosure generally relates to imaging, and, more specifically, to methods and systems that maintain a pristine window surface during image acquisition.

Image acquisition techniques and equipment can frequently be used to monitor various processes and to enable proactive control thereof. In many instances, an image acquisition unit, such as a camera, can be separated from a process environment by an electromagnetic radiation-transparent window so that the imaging optics are protected. The material comprising the electromagnetic radiation-transparent window may be chosen to be substantially compatible with the process environment, while still allowing electromagnetic radiation of a desired type or wavelength to pass through the window to the image acquisition unit. The term "optical transparency" and related variants thereof may be used synonymously herein as representing an electromagnetic radiation-transparent window that selectively transmits electromagnetic radiation of a desired wavelength. In more specific instances, the term "optical transparency" and related variants thereof may refer to transparency of a window material to visible electromagnetic radiation. Although an electromagnetic radiation-transparent window may be omitted, with a camera lens being directly exposed to the process environment, the risk of damaging the camera optics may be significantly increased in this configuration.

Over time, wear and tear, fouling and other issues can compromise the ability of an image acquisition unit to receive electromagnetic radiation from a process environment and to obtain a satisfactory image therefrom. For example, if an electromagnetic radiation-transparent window or camera lens becomes clouded, scratched, etched or fouled, a poor quality image or no image at all may be obtained, in which case the window or lens may need to be cleaned or replaced. Cleaning or replacing a window or lens can often be costly or difficult to perform. These issues may be particularly prevalent if the window or lens is physically inaccessible or if the process environment precludes ready access. In any event, unwanted alteration of a window or lens can be a highly undesirable event and can result in significant process downtime.

BRIEF DESCRIPTION OF THE DRAWINGS

The following figures are included to illustrate certain aspects of the present disclosure and should not be viewed as exclusive embodiments. The subject matter disclosed is capable of considerable modifications, alterations, combinations, and equivalents in form and function, as will occur to one having ordinary skill in the art and the benefit of this disclosure.

DETAILED DESCRIPTION

The present disclosure generally relates to imaging, and, more specifically, to methods and systems that maintain a pristine window surface during image acquisition.

One or more illustrative embodiments incorporating the features of the present disclosure are presented herein. Not all features of a physical implementation are necessarily described or shown in this application for the sake of clarity. It is to be understood that in the development of a physical implementation incorporating the embodiments of the present disclosure, numerous implementation-specific decisions may be made to achieve the developer's goals, such as compliance with system-related, business-related, government-related and other constraints, which may vary by implementation and from time to time. While a developer's efforts might be time-consuming, such efforts would be, nevertheless, a routine undertaking for one having ordinary skill in the art and the benefit of this disclosure.

As discussed above, various factors can lead to deterioration in the quality of images produced by an imaging system. In many instances, image deterioration can result from interaction of an electromagnetic radiation-transparent window or lens, such as an optically transparent window or lens, of the imaging system with its external environment, such as a process environment. This issue can be especially prevalent when analyzing samples within severe process environments that are prone to damaging or fouling a window or lens within an imaging system. Fluids circulated through a wellbore and produced therefrom, for example, can contain a complex mixture of components, including solids, that may be damaging to windows and other optical components. In an offshore drilling site, salt water-laden air can also be damaging to the optics of an imaging system.

In spite of the difficulties they can impose, analyses of solids and other substances within wellbore fluids can provide a wealth of useful information about an ongoing downhole process. For instance, analyses of drill cuttings by imaging techniques can provide information as to the effectiveness of a drilling operation. However, imaging in the presence of other wellbore fluids can be difficult due to other components that are circulated and co-produced with drill cuttings and their potential opacity to a desired electromagnetic radiation wavelength range. For example, a produced wellbore fluid may be opaque in the visible region of the electromagnetic spectrum and preclude obtaining visible light images of drill cuttings contained in the fluid.

The present inventors recognized that more efficient and extended imaging within wellbore fluids and other process fluids could be realized by protecting an electromagnetic radiation-transparent window or lens within an imaging system using a replaceable barrier that is also electromagnetic radiation-transparent. Specifically, the inventors recognized that by placing an electromagnetic radiation-transparent and movable barrier, such as an electromagnetic radiation-transparent and movable film, between an electromagnetic radiation-transparent window or lens and its sample environment, the window or lens may be protected by the barrier. The movable barrier allows the window or lens to maintain a pristine state during deployment, such that transparency to a desired electromagnetic radiation wavelength range is maintained and the image quality is not significantly impacted. The barrier may have a low cost and be easily replaced or reused, thereby protecting more expensive electronics and optics in the imaging system.

The present inventors further recognized that by making the barrier movable, better quality images may be obtained over the long term. Once a section of the barrier protecting the window or lens becomes damaged or fouled, it may be readily replaced by a new section of the barrier to allow image acquisition to continue unabated. The inventors identified suitable equipment and processes to ensure that the barrier is provided in a desired manner, as discussed hereinafter.

Furthermore, the movable barrier may also comprise a structure for limiting the particular wavelengths of electromagnetic radiation able to pass through the barrier. For example, the movable barrier may further comprise a polarizer or wavelength filter in order to limit the range of wavelengths transmitted. Thus, the movable barrier may also allow windows to be used that are transparent to electromagnetic radiation only over a limited wavelength range. Further, the limiting structure within the movable barrier may remove electromagnetic radiation arising from undesired wellbore or formation components that would otherwise be transmitted through the chosen window material, potentially compromising the ability to obtain images therefrom.

Figure 1:
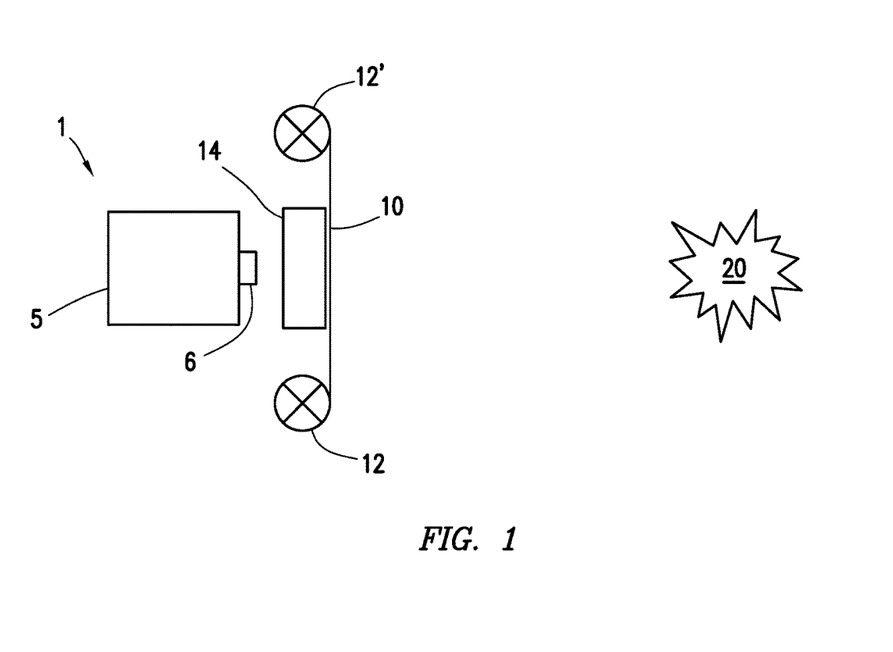
FIG. 1 shows a schematic of an illustrative imaging system having a movable barrier that protects an electromagnetic radiation-transparent window therein.

FIG. 1 shows a schematic of illustrative imaging system 1 having movable barrier 10 that protects electromagnetic radiation-transparent window 14 therein. Imaging system 1 includes image acquisition unit 5 and lens 6 connected thereto. When collecting visible light images, for example, image acquisition unit 5 may comprise a visible light camera. Other suitable types of cameras are described below. Electromagnetic radiation-transparent window 14 separates image acquisition unit 5 from its external environment. Suitable materials for forming electromagnetic radiation-transparent window 14 include, but are not limited to, glass, quartz, sapphire, plastics, and other electromagnetic radiation-transparent materials. In the case of visible light images, electromagnetic radiation-transparent window 14 may be substantially transparent to at least a portion of the visible light spectrum.

In the configuration depicted in FIG. 1, electromagnetic radiation-transparent window 14 is spaced apart from lens 6. However, without departing from the scope of FIG. 1, electromagnetic radiation-transparent window 14 and lens 6 may abut one another or be contiguous with one another. That is, in some embodiments, electromagnetic radiation-transparent window 14 may be omitted and lens 6 may be directly protected from its sampling environment by movable barrier 10, without departing from the scope of the present disclosure. Considered alternately, electromagnetic radiation-transparent window 14 may take the place of lens 6.

With continued reference to FIG. 1, electromagnetic radiation-transparent window 14 is further protected by movable barrier 10, which may be in the form of an electromagnetic radiation-transparent thin film. Electromagnetic radiation-transparent films may be transportable between first reel 12 and second reel 12' in order to maintain sufficient optical transparency through electromagnetic radiation-transparent window 14, as discussed further below. Optionally one or both of reels 12 and 12' may be heated in order to maintain movable barrier 10 in a sufficiently flexible state and to preclude ice formation thereon in cold sampling environments (e.g., through the use of air heating). Movable barrier 10 may include any suitable material that is sufficiently transparent to the electromagnetic radiation to be received by image acquisition unit 5. When visible light optical images are to be obtained with a camera, movable barrier 10 may comprise a polymer thin film such as, for example, polypropylene or polyethylene. Other suitable polymers for visible light imaging may include, for example, polytetrafluoroethylene, fluorinated polypropylene and fluorinated ethylene-propylene copolymer. Depending upon the chemical environment to which movable barrier 10 is to be exposed and the type of image to be obtained, other electromagnetic radiation-transparent polymers may also be suitable. For example, movable barrier glass films, polymer resins, polyesters and the like may comprise the movable barrier and/or lens 6.

In alternative configurations, movable barrier 10 may be disposed in a substantially planar structure that is rotatable (e.g., a rotatable disc) in order to expose a second section of movable barrier 10 to electromagnetic radiation-transparent window 14.

Solid particulate 20 may emit or reflect electromagnetic radiation that is received by image acquisition unit 5 and processed to form an image. The electromagnetic radiation may be visible light or infrared radiation, including near-infrared, mid-infrared, and/or far-infrared electromagnetic radiation. Accordingly, the image obtained by image acquisition unit 5 may be a visible light image, a thermal image, a spectrographically derived image, or the like. Although not depicted in FIG. 1, image acquisition unit 5 may be communicatively or operatively coupled to one or more of a data storage unit, a logic unit, or any combination thereof, any of which may operate under computer control. The computer may be operable to interpret an image obtained with image acquisition unit 5 and determine that movable barrier 10 is damaged, fouled, and/or needs to be cleaned (e.g., using a fixed or rotating brush to remove particles or sludge adhered to movable barrier 10).

Movable barrier 10 may protect electromagnetic radiation-transparent window 14 from fouling or like damage. Instead of electromagnetic radiation-transparent window 14 itself becoming fouled or damaged, a section of movable barrier 10 becomes damaged or fouled over time. Unlike electromagnetic radiation-transparent window 14, however, a second section of movable barrier 10 may replace the first section to maintain a pristine or near-pristine transmission pathway through electromagnetic radiation-transparent window 14.

More specifically, in the configuration of FIG. 1, movable barrier 10 can be transported or scrolled from first reel 12 to second reel 12' during operation of imaging system 1 (e.g., by rotating reels 12 and 12'), thereby replacing a damaged or fouled first section of movable barrier 10 with a pristine second section and allowing electromagnetic radiation of a desired wavelength range to continue to be received by image acquisition unit 5. Movable barrier 10 may be configured to be transported or scrolled continuously or discontinuously in order to maintain a pristine optical pathway. When transported continuously, the rate of transport may be modulated to maintain a sufficient degree of electromagnetic radiation transmission through electromagnetic radiation-transparent window 14. When transported discontinuously, movable barrier 10 may be transported at set time intervals or upon an automated determination that the image quality has deteriorated (e.g., upon buildup of a threshold amount of an interfering substance, or if the amount of electromagnetic radiation passing through electromagnetic radiation-transparent window 14 drops below a set level). Suitable time intervals for advancement may be determined based upon an anticipated time for fouling or damage to occur upon exposure to the particular environment to be sampled. In still other instances, a user may manually make a determination that the image quality has deteriorated and affect advancement of movable barrier 10. Control of the advancement of movable barrier 10 may occur in a wired or wireless configuration using appropriate hardware or software, or mechanical actuation techniques may also be used. Suitable equipment for actuating the transport of movable barrier 10 will be familiar to one having ordinary skill in the art.

In further embodiments, the system may notify a user when movable barrier 10 is at the end of its useful lifetime or is simply about to be exhausted and is in need of replacement. In some embodiments, replacement of movable barrier 10 may take place when drilling operations have ceased in order to minimize system downtime.

In more particular embodiments, the foregoing imaging systems may comprise a portion of an imaging system located at a wellhead. Accordingly, the imaging systems may be incorporated within a flow pathway extending from a wellbore to the earth's surface, where the imaging takes place external to the wellbore (i.e., on or above the earth's surface). The flow pathway may extend from the wellbore, or it may be in fluid communication with a flow pathway extending from the wellbore. In illustrative embodiments, imaging systems of the present disclosure may be used to perform analyses of drill cuttings at a wellhead external to a wellbore.

Figure 2:
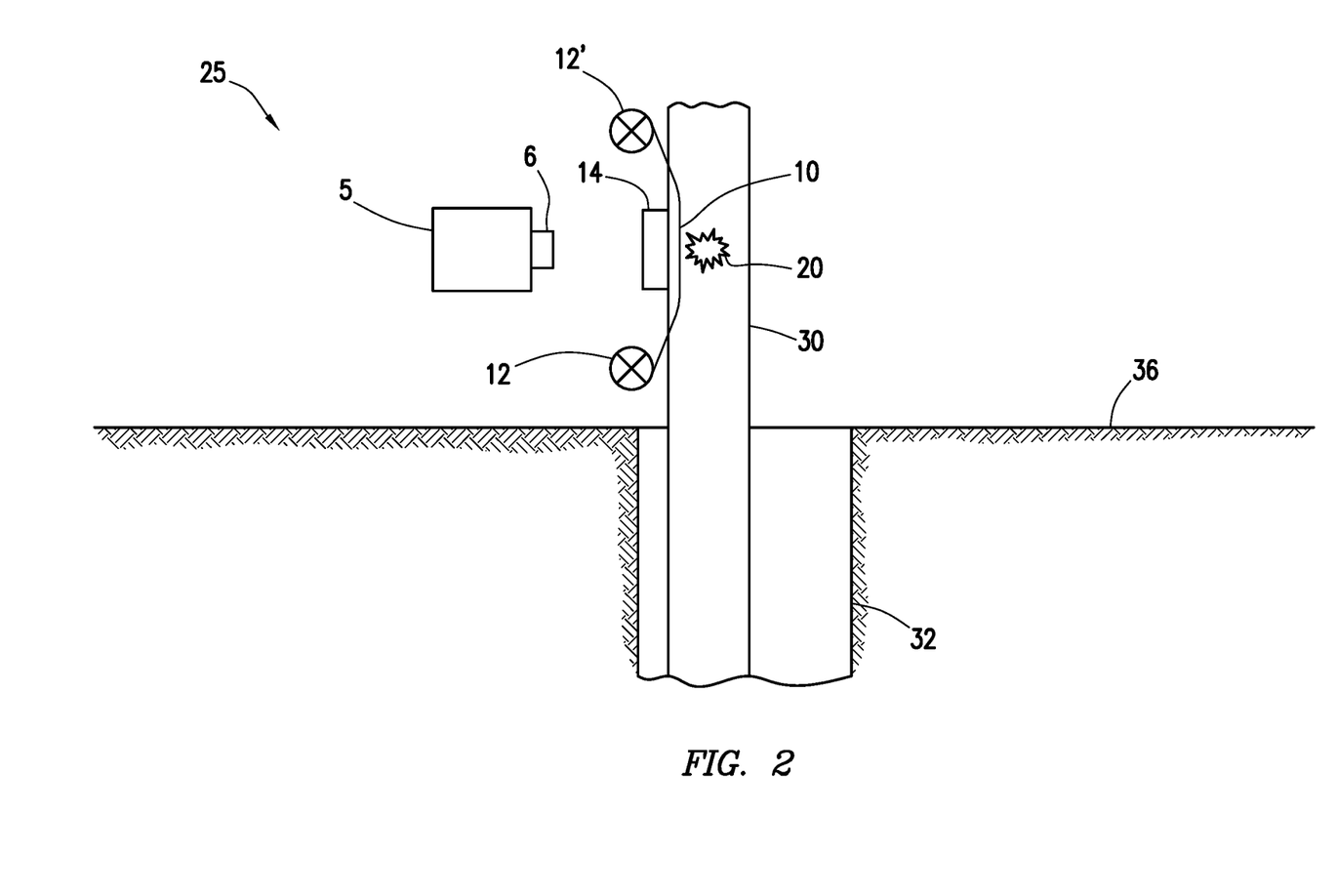
FIG. 2 shows a schematic of an illustrative imaging system having a movable barrier that protects an electromagnetic radiation-transparent window therein, where the imaging system is located at a wellhead.

FIG. 2 shows a schematic of an illustrative imaging system 25 having a movable barrier that protects an electromagnetic radiation-transparent window therein, where the imaging system is located at a wellhead. Imaging system 25 may be similar in many respects to imaging system 1 of FIG. 1 and may be better understood with reference thereto. Elements of FIG. 2 having a like function to those of FIG. 1 will be labelled with like reference characters and will generally not be described in detail again in the interest of brevity.

Referring to FIG. 2, flow pathway 30 extends from wellbore 32 or is otherwise in fluid communication with wellbore 32. For example, flow pathway 30 may be in fluid communication with wellbore 32 and provide low-pressure sampling of a wellbore fluid. Electromagnetic radiation-transparent window 14 establishes optical communication with flow pathway 30 external to wellbore 32 (i.e., above earth's surface 36). As in FIG. 1, image acquisition unit 5 may acquire an image of solid particulate 20, this time within flow pathway 30. Movable barrier 10 is provided from first reel 12 and is conveyed to second reel 12', as generally described above. In the configuration depicted in FIG. 2, movable barrier 10 is provided from first reel 12 external to flow pathway 30 in order to avoid exposing movable barrier 10 to substances that might otherwise compromise its optical integrity. Movable barrier 10 may be received at second reel 12' external to flow pathway 30, as depicted in FIG. 2, or alternately, second reel 12' may be disposed within flow pathway 30, if desired.

Figure 3:
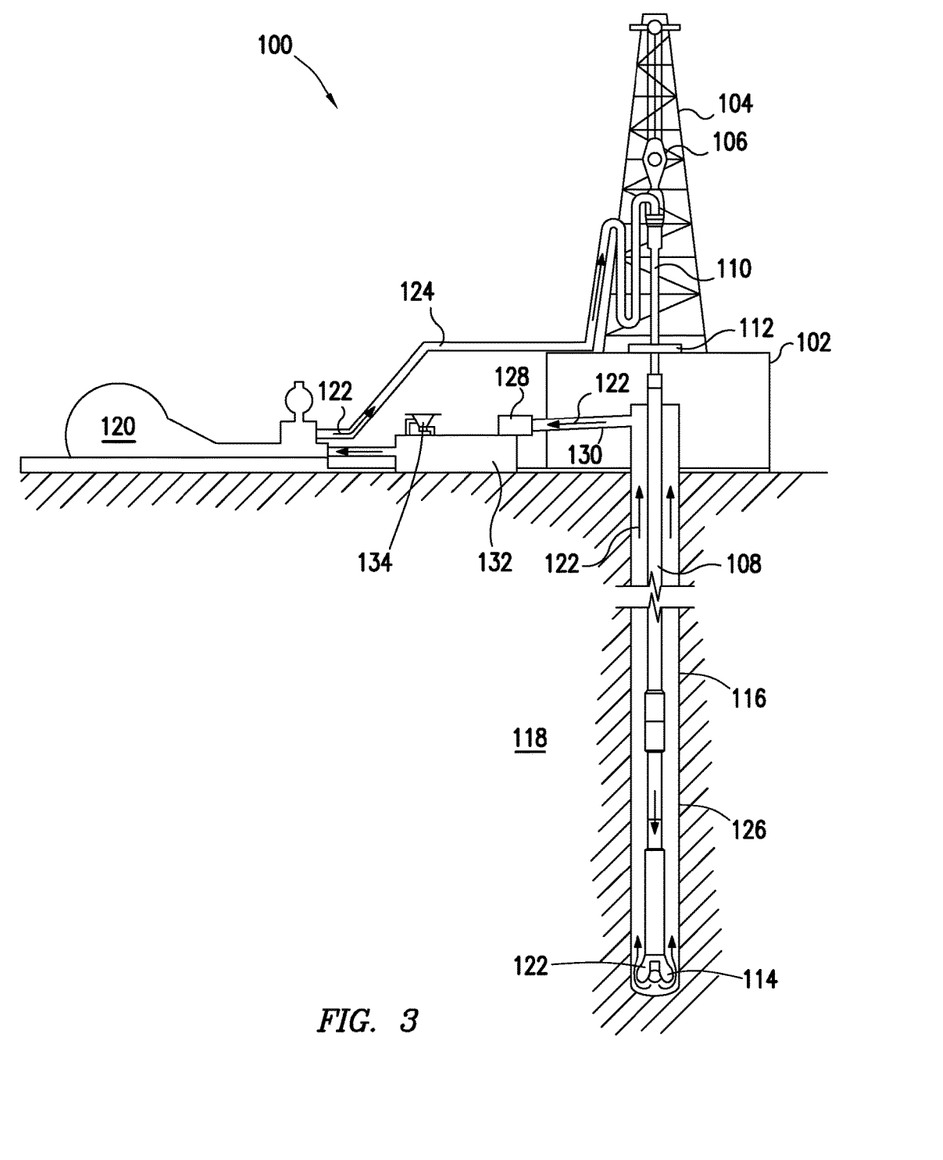
FIG. 3 shows a drilling assembly in which imaging systems of the present disclosure may be deployed.

In illustrative embodiments, the imaging systems described herein may be coupled to a drilling process assembly, as illustrated in FIG. 3. FIG. 3 shows a drilling assembly in which imaging systems of the present disclosure may be deployed. Deployment of the imaging systems may take place in any suitable location within drilling assembly 100, particularly at or downstream of the wellhead. While FIG. 3 generally depicts a land-based drilling assembly, one having ordinary skill in the art will readily recognize that the principles described herein are equally applicable to subsea drilling operations that employ floating or sea-based platforms and rigs, without departing from the scope of the disclosure.

As illustrated, drilling assembly 100 may include drilling platform 102 that supports derrick 104 having traveling block 106 for raising and lowering drill string 108. Drill string 108 may include, but is not limited to, drill pipe and coiled tubing, as generally known by one having ordinary skill in the art. Kelly 110 supports drill string 108 as it is lowered through rotary table 112. Drill bit 114 is attached to the distal end of drill string 108 and is driven either by a downhole motor and/or via rotation of drill string 108 from the well surface. As drill bit 114 rotates, it creates borehole 116 that penetrates various subterranean formations 118.

Pump 120 (e.g., a mud pump) circulates drilling fluid 122 through feed pipe 124 and to kelly 110, which conveys drilling fluid 122 downhole through the interior of drill string 108 and through one or more orifices in drill bit 114. Drilling fluid 122 is then circulated back to the surface via annulus 126 defined between drill string 108 and the walls of borehole 116. At the surface, the recirculated or spent drilling fluid 122 exits annulus 126 and may be conveyed to one or more fluid processing unit(s) 128 via interconnecting flow line 130. In some embodiments, the imaging systems of the present disclosure may be disposed along interconnected flow line 130 or at one or more of fluid processing unit(s) 128. After passing through fluid processing unit(s) 128, a "cleaned" drilling fluid 122 is deposited into nearby retention pit 132 (i.e., a mud pit). While illustrated as being arranged at the outlet of wellbore 116 via annulus 126, one having ordinary skill in the art will readily appreciate that fluid processing unit(s) 128 may be arranged at any other location in drilling assembly 100 to facilitate its proper function, without departing from the scope of the disclosure. Similarly, the imaging systems of the present disclosure may be disposed at any suitable location to attain satisfactory analyses of drill cuttings or other particulate solids of interest that are produced from borehole 116.

Drilling fluid 122 may be formulated in mixing hopper 134 that is communicably coupled to or otherwise in fluid communication with retention pit 132. Mixing hopper 134 may include, but is not limited to, mixers and related mixing equipment known to a person having ordinary skill in the art. In at least one embodiment, for example, there could be more than one retention pit 132, such as multiple retention pits 132 in series. Moreover, retention pit 132 may be representative of one or more fluid storage facilities and/or units where drilling fluid 122 may be stored, reconditioned, and/or regulated.

Drilling fluid 122 may directly or indirectly affect the components and equipment of drilling assembly 100. For example, drilling fluid 122 may directly or indirectly affect fluid processing unit(s) 128 which may include, but are not limited to, one or more of a shaker (e.g., shale shaker), a centrifuge, a hydrocyclone, a separator (including magnetic and electrical separators), a desilter, a desander, a separator, a filter (e.g., diatomaceous earth filters), a heat exchanger, and any fluid reclamation equipment. The imaging systems of the present disclosure may be located in proximity to any of these components. Fluid processing unit(s) 128 may further include one or more sensors, gauges, pumps, compressors, and the like used to store, monitor, regulate, and/or recondition the exemplary drilling fluids.

Drilling fluid 122 may directly or indirectly affect pump 120, which representatively includes any conduits, pipelines, trucks, tubulars, and/or pipes used to fluidically convey the drilling fluids downhole, any pumps, compressors, or motors (e.g., topside or downhole) used to drive the drilling fluids into motion, any valves or related joints used to regulate the pressure or flow rate of the drilling fluids, and any sensors (i.e., pressure, temperature, flow rate, etc.), gauges, and/or combinations thereof, and the like. Drilling fluid 122 may also directly or indirectly affect mixing hopper 134 and retention pit 132 and their assorted variations.

Drilling fluid 122 may also directly or indirectly affect the various downhole equipment and tools that may come into contact with the drilling fluids such as, but not limited to, drill string 108, any floats, drill collars, mud motors, downhole motors and/or pumps associated with drill string 108, and any MWD/LWD tools and related telemetry equipment, sensors or distributed sensors associated with drill string 108. Drilling fluid 122 may also directly or indirectly affect any downhole heat exchangers, valves and corresponding actuation devices, tool seals, packers and other wellbore isolation devices or components, and the like associated with wellbore 116. Drilling fluid 122 may also directly or indirectly affect drill bit 114, which may include, but is not limited to, roller cone bits, PDC bits, natural diamond bits, any hole openers, reamers, coring bits, and the like.

While not specifically illustrated herein, drilling fluid 122 may also directly or indirectly affect any transport or delivery equipment used to convey the drilling fluids to drilling assembly 100 such as, for example, any transport vessels, conduits, pipelines, trucks, tubulars, and/or pipes used to fluidically move the drilling fluids from one location to another, any pumps, compressors, or motors used to drive the drilling fluids into motion, any valves or related joints used to regulate the pressure or flow rate of the drilling fluids, and any sensors (i.e., pressure and temperature), gauges, and/or combinations thereof, and the like.

Accordingly, in illustrative embodiments, particle imaging systems described herein may comprise: a flow pathway extending from a wellbore; an electromagnetic radiation-transparent window external to the wellbore, establishing optical communication with the flow pathway; an image acquisition unit in optical communication with the flow pathway via the electromagnetic radiation-transparent window; and a movable barrier that is also electromagnetic radiation-transparent and is disposed between the electromagnetic radiation-transparent window and the flow pathway. The movable barrier allows electromagnetic radiation to pass through the electromagnetic radiation-transparent window to the image acquisition unit, while maintaining an optically pristine window surface and also protecting the image acquisition unit from its external environment.

In various embodiments, the movable barrier may abut the electromagnetic radiation-transparent window and be in fluid communication with the flow pathway. That is, in such embodiments, the movable barrier may be disposed within the flow pathway, as illustratively depicted in FIG. 2. By abutting the movable barrier with the electromagnetic radiation-transparent window, the likelihood of fouling or damaging the window upon contacting a material in the flow pathway may be significantly decreased. Instead, fouling or damage may occur to the section of the movable barrier that abuts the electromagnetic radiation-transparent window. In order to maintain transparency to a desired wavelength range of electromagnetic radiation, the imaging systems may further comprise a mechanism for transporting the movable barrier in order to expose a new section of the movable barrier to the electromagnetic radiation-transparent window.

In more particular embodiments, the image acquisition unit may be a camera. Suitable cameras may comprise a lens, other optics and processing controls for producing an image. Suitable cameras may include a camera type selected from a visible light camera, a near-infrared camera, a mid-infrared camera, a far-infrared camera, and any combination of these types of cameras. For example, by utilizing a visible light camera and an infrared camera for imaging, one may obtain a visible light image and a thermal image within the same field of view. The multiple image types may be beneficial in performing analyses of drill cuttings.

More specific examples of cameras may include, for example, charge coupled device cameras, and low light cameras. Suitable cameras for visible light imaging may include, for example, a pco 4000 CCD camera from Adept Turnkey Pty Ltd. with 4008×2672 pixel resolution for the visible light spectrum, a Piranha HS-80-08K40 camera or a Piranha HS-40-04K40 camera, also from Adept Turnkey Pty Ltd. For near-infrared imaging, an XEVA-FPA-1.7-640 camera from the LOT-Oriel Group Europe with an InGaAs array at 640×512 resolution can be used. For mid-infrared imaging, a VarioTHERM® InSb camera from JENOPTIK Optical Systems Inc. with an InSb array at 640×512 resolution can be used. For far-infrared detection, a Photon 640 camera from FLIR Systems, Inc. can be employed. It is to be recognized that the foregoing cameras represent illustrative examples of the types of cameras that may be suitably used in the embodiments of the present disclosure. Other suitable cameras can also be used and will be familiar to one having ordinary skill in the art. For example, suitable cameras may be chosen based upon their ability to obtain real-time images, near real-time images, and/or continuously acquired images.

In further embodiments, an illumination source may be present in order to improve image quality obtained from the camera. Suitable illumination sources may be dependent upon the type of camera employed, and may include, for example, white light sources, tungsten filament sources, infrared light sources, light emitting diodes, lasers and the like.

In further embodiments, at least one structure configured for modifying electromagnetic radiation may be disposed between the sample (i.e., a solids-containing fluid in the flow pathway) and the image acquisition unit. Suitable structures may include, for example, polarizers, filters, beam splitters, wavelength selective gratings, the like, and any combination thereof. The modifying structures may allow wavelengths of electromagnetic radiation unrelated to solids undergoing imaging from reaching the image acquisition unit. As discussed below, at least some of these modifying structures may be present in the movable barrier itself.

In more specific embodiments, the movable barrier may comprise an electromagnetic radiation-transparent film. Accordingly, in some embodiments, the imaging systems may further comprise a first reel and a second reel, between which the electromagnetic radiation-transparent film is transportable, as depicted in FIGS. 1 and 2. Other configurations for transporting an electromagnetic radiation-transparent movable barrier are also possible, such as an axially rotatable disc. Other suitable configurations may also include, for example, thin films in interchangeable frames, peel away films, and electrostatically attached films.

In other illustrative embodiments, an electromagnetic radiation-transparent film may comprise a continuous loop that is circulatable or scrollable between the first reel and the second reel. That is, in such embodiments, the same section of the electromagnetic radiation-transparent film may be disposed upon the electromagnetic radiation-transparent window multiple times in order to convey fouling and damage protection thereto.

In further embodiments, a cleaning mechanism for the electromagnetic radiation-transparent film may be present. The cleaning mechanism may clean the electromagnetic radiation-transparent film at any time after it leaves the electromagnetic radiation-transparent window. When transferring the electromagnetic radiation-transparent film to a second reel, the film may be cleaned before uptake on the second reel. In other illustrative embodiments, the electromagnetic radiation-transparent film wound upon the second reel may be recovered and cleaned after uptake on the reel. For example, the rotation direction of the first and second reels may be reversed in order to move the electromagnetic radiation-transparent film across the electromagnetic radiation-transparent window from the opposite direction, in which case cleaning of the film may be desirable. In the case of the electromagnetic radiation-transparent film being in the form of a continuous loop, cleaning of the film may take place at any location before a given section of the film is returned to the electromagnetic radiation-transparent window. Suitable cleaning mechanisms and processes for thin film materials will be familiar to one having ordinary skill in the art. For example, suitable cleaning mechanisms, may include brushes, compressed air, chemical baths, and/or the like. The system may further determine the effectiveness of the cleaning operation and determine if further cleaning is needed.

In more specific embodiments, the electromagnetic radiation-transparent film may comprise a polymer film. Suitable polymer films may comprise, for example, polyethylene films and/or polypropylene films. Other suitable polymer films may include, for example, polytetrafluoroethylene, fluorinated polypropylene and fluorinated ethylene-propylene copolymer. These polymer films may be particularly desirable due to their chemical resistance and transparency within the visible region of the electromagnetic spectrum. Other polymer films may also be suitable and can be identified based upon known properties of a given polymer, the anticipated chemical environment to which the polymer film will be exposed, as well as due to other considerations. Given the benefit of the present disclosure, one having ordinary skill in the art will be able to choose a suitable polymer film for deployment in a particular situation.

In still further embodiments, the electromagnetic radiation-transparent film may further comprise at least one feature operable to control wavelengths of electromagnetic radiation that are transmitted through the film. In illustrative embodiments, polarizers, filters, and/or wavelength selective slits or gratings may be defined in a film in order to further tailor the wavelengths of electromagnetic radiation that are transmitted therethrough. In some or other illustrative embodiments, a dopant may be present in the film in order to tailor the wavelengths of electromagnetic radiation that are transmitted therethrough. In some embodiments, nanoparticles may comprise a suitable dopant due to their ability to strongly absorb certain wavelengths of electromagnetic radiation while only inducing minimal scattering effects.

In more specific embodiments, the illustrative imaging systems described herein may be configured to obtain an image of drill cuttings. In some embodiments, the drill cuttings may be imaged while they are in a fluid phase transiting through the flow pathway. In other illustrative embodiments, the drill cuttings may be imaged while they are in a static condition. In illustrative embodiments, the drill cuttings may be collected on a drilling mud screen and then undergo imaging. Accordingly, in more specific embodiments, a drilling mud screen may comprise at least a portion of the flow pathway described above. Other suitable locations for static imaging within the flow pathway may include, for example, at a shaker (e.g., a shale shaker) or other solid particle removal system.

In further embodiments, the image acquisition unit may be configured to acquire an image from within the flow pathway upon receipt of electromagnetic radiation having a triggering wavelength signature. That is, the image acquisition may be configured (e.g., through incorporation of appropriate sensing technology) such that it does not acquire images continuously. Instead, the image acquisition unit may acquire images when it senses a triggering event, such as a particular wavelength and/or intensity of electromagnetic radiation passing through the electromagnetic radiation-transparent window. In some embodiments, the triggering electromagnetic radiation may be inherent to a substance that is being imaged and analyzed by the system. In other various embodiments, the triggering electromagnetic radiation may result from addition of a substance to the fluid before the fluid transits the flow pathway. In illustrative embodiments, the substance may comprise a dye, which emits characteristic wavelengths of triggering electromagnetic radiation. Configuration of the imaging systems of the present disclosure to accommodate the spectral properties of a given dye may be undertaken by one having ordinary skill in the art. In further embodiments, receipt of electromagnetic radiation from the dye may be used to trigger replacement of the first section of the movable barrier with the second section of movable barrier, or to validate operation of the system using particulates have a known interaction in the presence of the dye. Suitable dyes and other tracers are described in greater detail hereinbelow.

The imaging systems and processes of the present disclosure can be further advantageous in a number of respects. They may allow for continuous monitoring and imaging to take place without substantial downtime for cleaning and replacement of system optics. In addition, they may allow for images of solid particulates to be acquired and analyzed in real-time or near real-time. Analyses obtained in real-time or near real-time may allow at least some degree of proactive process control to be realized. Conventional analyses of drill cuttings, in contrast, are typically conducted by withdrawing a sample from the flow path and acquiring images offline, not to mention further delays for conducting analyses of the acquired images. Accordingly, the imaging systems and processes of the present disclosure can allow faster and more efficient analyses of drill cuttings and other solid particulates to be realized. Techniques for performing analyses of drill cuttings are beyond the scope of this disclosure and will not be described in any further detail herein.

In other various embodiments, the illustrative imaging systems described herein may be used to acquire an image of solids within a fluid received from a wellbore. In some embodiments, the methods may comprise: receiving a fluid in a flow pathway extending from a wellbore, the fluid containing a plurality of solids; acquiring an image of the solids using an image acquisition unit that is in optical communication with the flow pathway via an electromagnetic radiation-transparent window, the electromagnetic radiation-transparent window being located external to the wellbore; wherein a first section of a movable barrier is disposed between the electromagnetic radiation-transparent window and the flow pathway, the movable barrier also being electromagnetic radiation-transparent; allowing an interfering substance to build up on the first section of the movable barrier; and replacing the first section of the movable barrier with a second section of the movable barrier upon buildup of the interfering substance.

Interfering substances that may build up on the movable barrier are not believed to be particularly limited and can include any substance that detrimentally influences the passage of electromagnetic radiation through the movable barrier to the image acquisition unit. Interfering substances may vary from application to application, and in non-limiting embodiments may comprise a coating of formation fines, an opaque polymer, tar, asphaltenes, oil, a weighting agent, or any combination thereof. Scratches or like damage to the movable barrier will also be considered to represent an interfering substance within the context of the present disclosure. To the extent possible, a material comprising the movable barrier may be chosen to limit adherence of or damage by particular interfering substances that may be present in a fluid received in the flow pathway.

By replacing the first section of the movable barrier with the second section of the movable barrier according to the embodiments of the present disclosure, a pristine or near pristine electromagnetic radiation-transparent window surface may be maintained in order to promote image acquisition from within the flow pathway. In some embodiments, replacing the first section of the movable barrier with the second section of the movable barrier may comprise transporting an electromagnetic radiation-transparent film from a first reel to a second reel. In further embodiments, a continuous loop of the electromagnetic radiation-transparent film may by circulated between the first reel and the second reel in order to maintain a pristine or near pristine electromagnetic radiation-transparent window surface for image acquisition. In still additional embodiments, the methods may further comprise cleaning the interfering substance from the first section of the electromagnetic radiation-transparent film after it is replaced by the second section of the electromagnetic radiation-transparent film.

Operation of the imaging systems may continue until a supply of the electromagnetic radiation-transparent film on the first reel has been exhausted. Once the electromagnetic radiation-transparent film has been transported from the first reel to the second reel, it may be cleaned and reused, or it may be removed and discarded. When loading the imaging system with new electromagnetic radiation-transparent film is problematic or expensive (e.g., when using a film having wavelength selective slits or other features defined therein), cleaning and reuse of the electromagnetic radiation-transparent film may be desirable. Reuse of the electromagnetic radiation-transparent film may comprise reversing the rotation direction of the reels, or removing the second reel from the imaging system and reloading it in the position of the first reel. In some embodiments, the electromagnetic radiation-transparent film may be in the form of a continuous loop that is transported between the first reel and the second reel, with cleaning of a section of the electromagnetic radiation-transparent film occurring before it is returned to the electromagnetic radiation-transparent window. In various embodiments, cleaning an interfering substance from a first section of the electromagnetic radiation-transparent film may take place after it is replaced by the second section of the electromagnetic radiation-transparent film.

In still other embodiments, once the electromagnetic radiation-transparent film has been collected at the second reel and cleaned, the direction of the reel rotation may be reversed to provide for continued imaging. Accordingly, a continuous supply of the electromagnetic radiation-transparent film may be provided in this manner without placing it in a continuous loop.

Imaging within the flow pathway may take place continuously or discontinuously. Continuous image acquisition techniques may require storage and analysis of significant amounts of extraneous data that may not be of interest for performing a particular analysis. Hence, discontinuous acquisition of images by the image acquisition unit may be especially desirable. When images are acquired discontinuously, imaging may be performed upon receipt of electromagnetic radiation having a triggering wavelength signature, as discussed further below. Additional discontinuous imaging strategies are discussed above.

In more particular embodiments, the triggering wavelength signature may be produced through the use of a dye. Suitable dyes are discussed hereinbelow. Other tracers and like substances may be used similarly. Accordingly, in some embodiments of the present disclosure, imaging methods may further comprise introducing the dye into the wellbore. The dye may be introduced into the wellbore at any suitable location or point in time. In some embodiments, the dye may be present in the drilling fluid and be introduced while drilling the wellbore. In other various embodiments, the dye may be introduced to the wellbore in a viscous sweep. The viscous sweep represents a fluid pill that serves to remove residual solids from the wellbore during drilling or at the completion of drilling. Analysis of drill cuttings within a viscous sweep may allow one to gain insight into the effectiveness of a drilling process, as well as into the effectiveness of the viscous sweep itself. In addition, analysis of the electromagnetic radiation received from a dye may be used to determine if the movable barrier is fouled, damaged or otherwise compromised and needs to be replaced, or as a trigger to initiate replacement of the first section of the movable barrier with the second section of the movable barrier.

By introducing a dye within a viscous sweep, one may, if desired, only acquire images within the flow pathway when the viscous sweep and any accompanying solids are transiting the flow pathway. That is, by actuating the imaging system only when detecting a set of wavelengths produced by the dye, the amount of extraneous imaging data may be significantly decreased. The dye and/or the electromagnetic radiation-transparent window may be chosen such that electromagnetic radiation emitted by the dye is transmitted through the electromagnetic radiation-transparent window.

In more particular embodiments, the dye may be chosen to interact with solids that are removed from the wellbore in the fluid, such as drill cuttings within a viscous sweep. For example, in some embodiments, the dye may comprise a fluorescent dye, a number of which will be familiar to one having ordinary skill in the art. In some embodiments, the spectral signature of the dye may change when it interacts with solids produced from the wellbore. For example, when the dye is not effectively interacting with the solids in the fluid, the dye may be quenched, but it may no longer be quenched when effectively interacting with the solids in the wellbore fluid. The reverse may also be the case. Furthermore, the dye may be chosen to adhere to specific components comprising the mineralogy of a subterranean formation penetrated by the wellbore. For example, the dye may be chosen for its ability to adhere to a carbonate mineral when a carbonate formation is being drilled. By choosing the dye to interact with or adhere to particular types of solids, the systems and methods of the present disclosure may be configured to ignore solids that are not of interest for a particular analysis (e.g., sand).

In addition to dyes, other suitable substances for actuating the imaging systems of the present disclosure may include other substances that emit characteristic electromagnetic radiation and are detectable in extremely low quantities, such as radioisotope tracers, for example. Upon detecting a characteristic emission of a radioisotope (e.g., a gamma emission), imaging of a fluid in the flow pathway may take place.

Embodiments disclosed herein include:

A. Particle imaging systems. The imaging systems comprise: a flow pathway extending from a wellbore; an electromagnetic radiation-transparent window external to the wellbore, establishing optical communication with the flow pathway; an image acquisition unit in optical communication with the flow pathway via the electromagnetic radiation-transparent window; and a movable barrier that is also electromagnetic radiation-transparent and is disposed between the electromagnetic radiation-transparent window and the flow pathway.

B. Imaging methods. The methods comprise: receiving a fluid in a flow pathway extending from a wellbore, the fluid containing a plurality of solids; acquiring an image of the solids using an image acquisition unit that is in optical communication with the flow pathway via an electromagnetic radiation-transparent window, the electromagnetic radiation-transparent window being located external to the wellbore; wherein a first section of a movable barrier is disposed between the electromagnetic radiation-transparent window and the flow pathway, the movable barrier also being electromagnetic radiation-transparent; allowing an interfering substance to build up on the first section of the movable barrier; and replacing the first section of the movable barrier with a second section of the movable barrier upon buildup of the interfering substance.

Each of embodiments A and B may have one or more of the following additional elements in any combination:

Element 1: wherein the movable barrier abuts the electromagnetic radiation-transparent window and is in fluid communication with the flow pathway.

Element 2: wherein the image acquisition unit is a camera.

Element 3: wherein a lens comprising the camera is spaced apart from the electromagnetic radiation-transparent window.

Element 4: wherein the electromagnetic radiation-transparent window comprises a lens comprising the camera.

Element 5: wherein the camera comprises a camera type selected from the group consisting of a visible light camera, a near-infrared camera, a mid-infrared camera, a far-infrared camera, and any combination thereof.

Element 6: wherein the movable barrier comprises an electromagnetic radiation-transparent film, the imaging system further comprising a first reel and a second reel between which the electromagnetic radiation-transparent film is transportable.

Element 7: wherein the electromagnetic radiation-transparent film comprises a continuous loop that is circulatable between the first reel and the second reel.

Element 8: wherein the particle imaging system further comprises: a cleaning mechanism for the electromagnetic radiation-transparent film.

Element 9: wherein the electromagnetic radiation-transparent film further comprises at least one feature to control wavelengths of electromagnetic radiation transmitted through the film, the at least one feature being selected from the group consisting of a dopant, a plurality of wavelength-selective slits, and any combination thereof.

Element 10: wherein the electromagnetic radiation-transparent film comprises a polymer film.

Element 11: wherein the polymer film comprises a polyethylene film or a polypropylene film.

Element 12: wherein the image acquisition unit is configured to acquire an image from within the flow pathway upon receipt of electromagnetic radiation having a triggering wavelength signature.

Element 13: wherein a drilling mud screen comprises at least a portion of the flow pathway.

Element 14: wherein replacing the first section of the movable barrier with the second section of the movable barrier comprises transporting the electromagnetic radiation-transparent film from a first reel to a second reel.

Element 15: wherein the electromagnetic radiation-transparent film comprises a continuous loop that is circulated between the first reel and the second reel.

Element 16: wherein the method further comprises: cleaning the interfering substance from the first section of the electromagnetic radiation-transparent film after it is replaced by the second section of the electromagnetic radiation-transparent film.

Element 17: wherein the image of the solids is acquired upon receiving electromagnetic radiation having a triggering wavelength signature.

Element 18: wherein the triggering wavelength signature is produced by a dye, the method further comprising introducing the dye into the wellbore.

Element 19: wherein the dye interacts with at least a portion of the solids in the fluid to produce the triggering wavelength signature.

Element 20: wherein the dye is introduced into the wellbore in a viscous sweep.

Element 21: wherein the first section of the movable barrier is replaced by the second section of the movable barrier upon buildup of a threshold amount of the interfering substance on the first section of the movable barrier.

Element 22: wherein the first section of the movable barrier is automatically replaced by the second section of the movable barrier upon buildup of the threshold amount.

Element 23: wherein the first section of the movable barrier is replaced by the second section of the movable barrier at a set time interval.

By way of non-limiting example, exemplary combinations applicable to A and B include:

The imaging system of A in combination with elements 1 and 2.

The imaging system of A in combination with elements 1 and 3.

The imaging system of A in combination with elements 2 and 3.

The imaging system of A in combination with elements 2 and 6.

The imaging system of A in combination with elements 6 and 9.

The imaging system of A in combination with elements 3 and 12.

The method of B in combination with elements 1 and 2.

The method of B in combination with elements 1 and 3.
The method of B in combination with elements 2 and 3.
The method of B in combination with elements 3 and 6.
The method of B in combination with elements 2 and 6.
The method of B in combination with elements 6 and 9.
The method of B in combination with elements 3 and 12.
The method of B in combination with elements 6 and 14.
The method of B in combination with elements 12 and 17.
The method of B in combination with elements 17 and 18.
The method of B in combination with elements 18 and 20.
The method of B in combination with elements 14 and 21.
The method of B in combination with elements 21 and 22.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the specification and attached claims are approximations that may vary depending upon the desired properties sought to be obtained by the embodiments of the present disclosure. At the very least, and not as an attempt to limit the application of the doctrine of equivalents to the scope of the claim, each numerical parameter should at least be construed in light of the number of reported significant digits and by applying ordinary rounding techniques.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The disclosure illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. A particle imaging system comprising:
a transparent window external to a wellbore and establishing optical communication with a flow pathway extending from the wellbore;
an image acquisition unit in optical communication with the flow pathway via the transparent window;
a transparent movable film that forms a barrier between the transparent window and the flow pathway; and
a first reel and a second reel between which the transparent movable film is transportable.

2. The particle imaging system of claim 1, wherein the transparent movable film abuts the transparent window and is in fluid communication with the flow pathway.

3. The particle imaging system of claim 1, wherein the image acquisition unit comprises a lens that is spaced apart from the transparent window.

4. The particle imaging system of claim 3, wherein the transparent window is a lens of the image acquisition unit.

5. The particle imaging system of claim 1, wherein the transparent movable film comprises a continuous loop configured to scroll between the first reel and the second reel.

6. The particle imaging system of claim 1, further comprising a cleaning mechanism for the transparent movable film.

7. The particle imaging system of claim 1, wherein transparent movable film includes at least one of a dopant and a plurality of wavelength-selective slits.

8. A particle imaging system comprising:
a flow pathway extending from a wellbore;
an electromagnetic radiation-transparent window external to the wellbore and establishing optical communication with the flow pathway;
an image acquisition unit in optical communication with the flow pathway via the electromagnetic radiation-transparent window; and
a movable barrier that is also electromagnetic radiation-transparent and is disposed between the electromagnetic radiation-transparent window and the flow pathway.

9. The particle imaging system of claim 8, wherein the movable barrier abuts the electromagnetic radiation-transparent window and is in fluid communication with the flow pathway.

10. The particle imaging system of claim 8, wherein the image acquisition unit is a camera.

11. The particle imaging system of claim 10, wherein a lens comprising the camera is spaced apart from the electromagnetic radiation-transparent window.

12. The particle imaging system of claim 10, wherein the electromagnetic radiation-transparent window is a lens of the camera.

13. The particle imaging system of claim 10, wherein the camera comprises a camera type selected from the group consisting of a visible light camera, a near-infrared camera, a mid-infrared camera, a far-infrared camera, and any combination thereof.

14. The particle imaging system of claim 8, wherein the image acquisition unit acquires an image from within the flow pathway upon receipt of electromagnetic radiation having a triggering wavelength signature.

15. The particle imaging system of claim 8, wherein a drilling mud screen comprises at least a portion of the flow pathway.

16. A system, comprising:
a flow pathway extending from a wellbore, the flow pathway configured to contain a fluid containing a plurality of solids;
an image acquisition unit that is in optical communication with the flow pathway via an electromagnetic radiation-transparent window and that is configured to acquire an image of the solids, the electromagnetic radiation-transparent window being located external to the wellbore; and a movable barrier also being electromagnetic radiation-transparent, wherein a first section of the movable barrier is configured to be disposed between the electromagnetic radiation-transparent window and the flow pathway and to be replaced with a second section of the movable barrier upon buildup of an interfering substance on the first section of the movable barrier.

17. The system of claim 16, wherein the movable barrier abuts the electromagnetic radiation-transparent window and is in fluid communication with the flow pathway.

18. The system of claim 16, wherein the image acquisition unit comprises at least one of a visible light camera, a near-infrared camera, a mid-infrared camera, and a far-infrared camera.

19. The system of claim 16, wherein the movable barrier comprises an electromagnetic radiation-transparent film.

20. The system of claim 16, wherein the image acquisition unit is configured to acquire an image from within the flow pathway upon receipt of electromagnetic radiation having a triggering wavelength signature.

\* \* \* \* \*